United States Patent
Schnell et al.

(10) Patent No.: US 6,346,084 B1
(45) Date of Patent: Feb. 12, 2002

(54) MEASURING VASCULAR ACCESS PRESSURE

(75) Inventors: William J. Schnell, Libertyville, IL (US); Gary Leeman; David S. Utterberg, both of Seattle, WA (US)

(73) Assignee: DSU Medical Corporation, Las Vegas, NV (US)

( * ) Notice: Subject to any disclaimer, the term of this patent is extended or adjusted under 35 U.S.C. 154(b) by 0 days.

(21) Appl. No.: 09/479,962

(22) Filed: Jan. 10, 2000

(51) Int. Cl.⁷ ............................................. A61B 5/00
(52) U.S. Cl. .................................. 600/561; 600/485
(58) Field of Search ........................... 600/504, 485, 600/561; 604/86, 87, 158, 164, 166, 411, 506, 507, 508, 513, 905

(56) References Cited

U.S. PATENT DOCUMENTS

| | | | | |
|---|---|---|---|---|
| 3,817,085 A | * | 6/1974 | Stubbs | 73/23.2 |
| 4,493,693 A | * | 1/1985 | Bilstad et al. | 604/6.09 |
| 5,032,116 A | * | 7/1991 | Peterson et al. | 604/168.01 |
| 5,046,509 A | * | 9/1991 | Kater | 600/577 |
| 5,454,374 A | | 10/1995 | Omachi | 600/486 |
| 5,501,674 A | * | 3/1996 | Trombley, III et al. | 604/247 |
| 5,807,356 A | * | 9/1998 | Finch, Jr. et al. | 604/284 |
| 5,855,230 A | * | 1/1999 | Guala et al. | 138/89 |

OTHER PUBLICATIONS

Brochure—Medisystems Patient–Transducer Protector for Hemodialysis Dec. 1999.
Brochure—Medisystems Ancillary Products, May 1998.

* cited by examiner

*Primary Examiner*—John P. Lacyk
*Assistant Examiner*—Charles Marmor, II
(74) *Attorney, Agent, or Firm*—Seyfarth Shaw

(57) ABSTRACT

Access pressure for the vascular system is measured through a first tube, which is connected to the vascular system of a patient. The method comprises the following steps: connecting one end of pressure tubing to an outer end of the first tube with a member blocking the flow of blood through at least part of the pressure tubing, while permitting the passage of air therethrough, to attenuate pressure pulses through the tubing. One connects the other end of the tubing to a pressure gauge. Thus, pressure sensed from the vascular system is read by the gauge. Preferably, the internal volume of the pressure tubing is less than the internal volume of the first tube. Thus, pressurized blood entering the first tube as the pressure is read does not advance completely through the first tube. This can permit reuse of the pressure tubing, and also permits the pressure tubing to be of a substantial length so that the gauge may be manually held at approximately the patient's heart level as the vascular system pressure is being read.

31 Claims, 2 Drawing Sheets

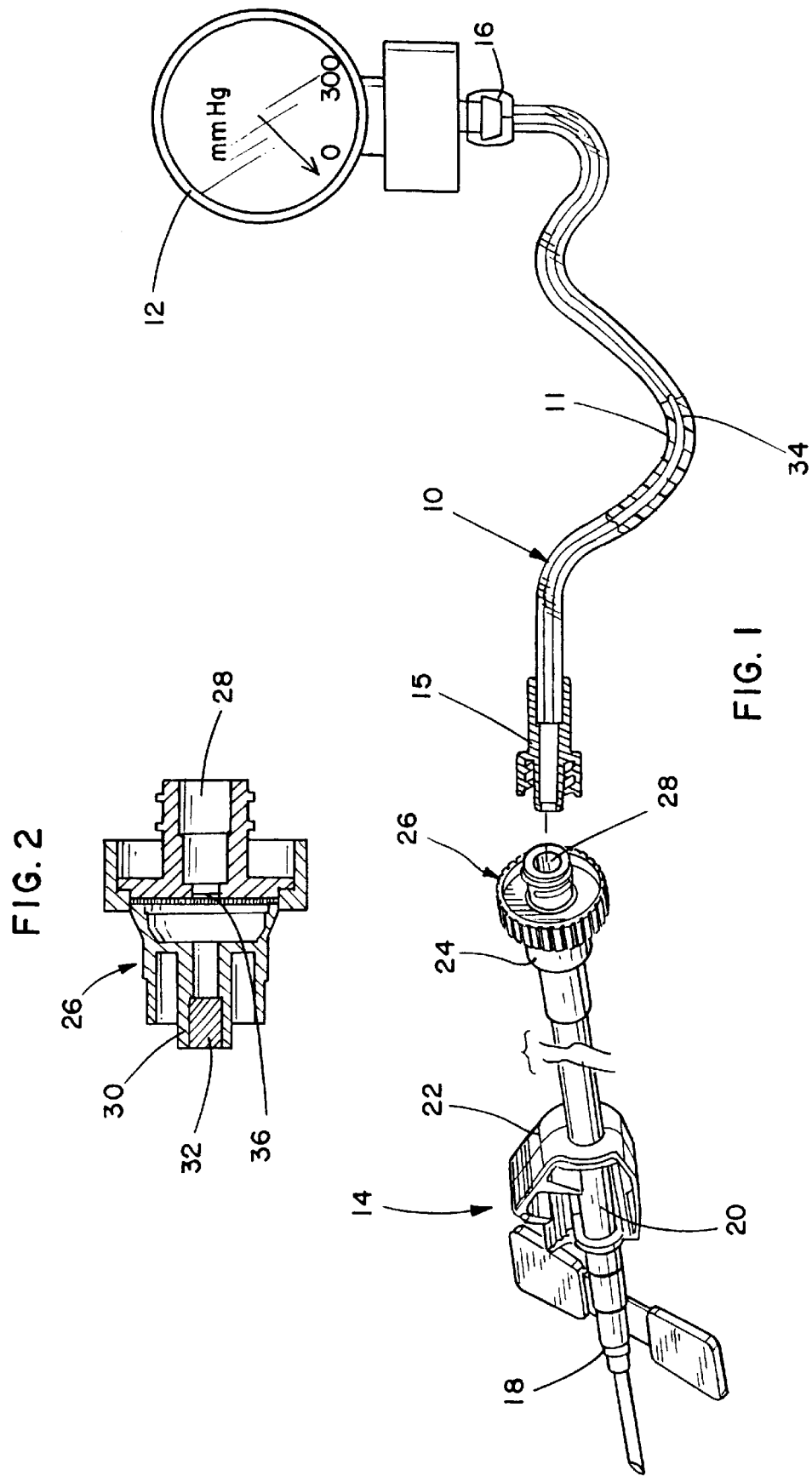

MEASURING VASCULAR ACCESS PRESSURE

BACKGROUND OF THE INVENTION

In the field of hemodialysis and other techniques where blood is removed from a patient for processing and then returned, it is important to periodically assess the blood flow rate through a fistula, graft, or catheter to monitor the onset of stenosis. This is often accomplished by the reading of access pressures through the venous and arterial fistula needles, for example. Early detection of stenosis in a fistula, graft, implantable port, or a catheter can permit low cost repairs to be made. On the other hand, if these problems are ignored or not detected, the cost of the revision or replacement of the fistula, graft, implantable port, or catheter can be very high and burdensome to the patient.

As shown in Omachi U.S. Pat. No. 5,454,374, access pressures may be determined through volumetric manipulations involving the determination of a pressure head height of blood in a visual manner. Alternatively, clinicians rely on a stop flow methodology using a blood flow line, which has technical problems. Also gauges on the dialysis machine are used to estimate pressure, which technique is imprecise. In these latter techniques, head height issues contribute to inaccuracy even when the machines provide a desirable, electronically dampened pressure reading.

It would be desirable to directly read the access pressure through a fistula needle, for example, before a blood tubing set is attached, which blood tubing set communicates between a fistula set in communication with the patient's vascular system and a membrane dialyzer. In doing this, it is important to isolate the sterile fistula needle set from a connected, unsterile pressure gauge. Also, there is a need to dampen the pressure pulse, which is naturally provided by the pulsatile flow of blood in the patient, to provide a mean pressure reading which is not strongly subject to inaccuracy due to head height variations. Ideally, the reading could be taken at about the level of the heart.

Furthermore, there is a need for such a device to control the flow of blood into the fistula set as pressure is measured, so that it does not enter into contact with a microporous barrier, which is typically present to protect the patient from bacterial contamination. Also, the system needs to have a substantial length to allow easy positioning and reading of the pressure gauge.

By this invention, the above needs are met in an inexpensive manner that is easy to use with relatively little training, so that patients can be monitored to detect the early onset of stenosis in a fistula, graft, implantable port, or catheter which is permanently implanted in connection with the vascular system of the patient.

DESCRIPTION OF THE INVENTION

By this invention, a method is provided of measuring access pressure through a first tube which is flow-connected to the vascular system of a patient. The method comprises the steps of: connecting one end of pressure tubing to an outer end of the first tube, with a member blocking the flow of blood through at least part of the pressure tubing while permitting the passage of air therethrough, to suppress or damp pressure pulses or oscillations through the tubing. One connects the other end of the pressure tubing to a pressure gauge. Thus, upon opening access through the first tube to the vascular system, blood flows into the first tube and compresses the air in the connected first tube and pressure tubing, plus the connected gauge, causing pressure from the vascular system to be readable by the gauge while the pressure pulses are attenuated in a simple, nonelectronic manner.

Preferably, the "member" mentioned above is a microporous member, typically a microporous block or plug positioned within or adjacent to the pressure tubing and capable of providing the damping or attenuation of the pulsatile nature of the pressure from the patient's cardiovascular system at the gauge.

Preferably, the internal volume of the pressure tubing is less than the internal volume of the first tube. As the result of this, pressurized blood entering an empty first tube as the pressure is read does not advance completely through the first tube before it is halted by compression of the initial air in the first tube and the pressure tubing, as well as the residual volume of air within the pressure gauge. This may be accomplished by providing pressure tubing which has a connector at each end, the tubing having a single lumen of reduced diameter from normal flexible tubing, which lumen diameter is typically no more than about one third of the outer diameter of the tubing. Thus, the internal volume of the pressure tubing can be less than the internal volume of the first tube even if the length of the pressure tubing is greater than the length of the first tube, which situation is preferred so that there is adequate tube length to conveniently hold a pressure gauge and to position it at approximately the level of the patient's heart and to read it with ease, and also to reduce the chance that the fistula needle connection to the patient's fistula is disturbed as the pressure gauge is connected and handled.

Preferably, the set which defines the pressure tubing carries a microporous member which is capable of preventing the passage of bacteria therethrough. This can be a second microporous member if desired, above and beyond the microporous plug described above which suppresses pressure oscillations through the pressure tubing, thus attenuating the pressure pulses. A conventional 0.2 micron bacterial filter may be used. This uniquely provides both flow blocking and aseptic conditions with commercially available materials.

Alternatively, the microporous member may be a plug which has a bacteria blocking capability similar to conventional 0.2 micron bacterial filters. Also, a membrane-type bacterial filter may have pores that are small enough to provide the desired attenuation of pressure pulses through the pressure tubing, to facilitate reading of the gauge.

Also, if desired, the pressure tubing may have a bore which is sufficiently narrow and of a length to provide the desired pressure pulse attenuation through the tubing without the need for a porous plug so that, typically, only a bacteria blocking filter membrane is provided, as needed, to protect the patient from bacterial contamination through connection to a nonsterile pressure gauge.

Thus, the objectives described above may be achieved by a structurally simple, inexpensive method and apparatus, as described herein.

DESCRIPTION OF THE DRAWINGS

FIG. 1 is an exploded plan view of a flexible, tubular set in accordance with this invention, being connected to a conventional fistula set, which is shown to carry a connector housing which contains the microporous member;

FIG. 2 is a longitudinal sectional view of the connector housing of FIG. 1; and

DESCRIPTION OF SPECIFIC EMBODIMENTS

Figure 3:
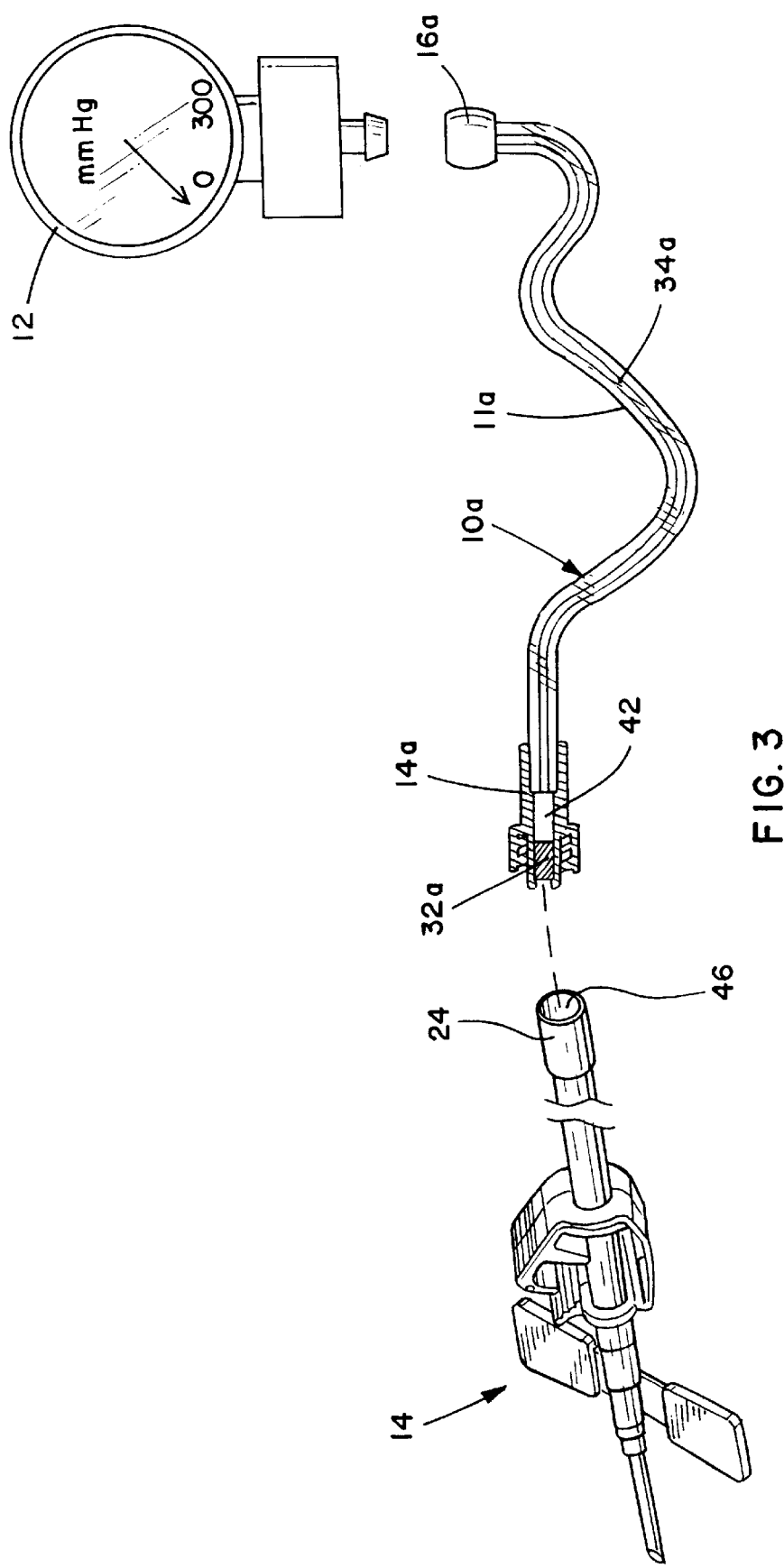
FIG. 3 is a second embodiment of the flexible tubular set of this invention, for connection with a conventional fistula set.

Referring to FIGS. 1 and 2, flexible tubular set 10 is shown, for connection between a pressure gauge 12 and a conventional fistula set 14 for tubular connection with the vascular system of a patient. Set 14 is specifically shown to be a conventional fistula set having a winged needle 18, a length of flexible tubing 20, a squeeze clamp 22, and a female luer connector 24. Luer connector 24 is shown to be in connection with a separate housing 26 that carries a pair of microporous members as discussed below.

Tubular set 10 comprises a length of pressure tubing 11 having connectors 15, 16 respectively at each end. Connector 15 comprises a male luer lock connector typically of conventional design, for connecting with a female luer connector.

The complete system, connected to fistula set 14, will comprise housing 26 and set 10 connected altogether, with set 10 being joined through conventional connector 16 to a commercially available pressure gauge 12.

FIG. 2 shows housing 26 to comprise female luer connector 28 on one side for connecting with male luer 15. Male luer 30 is on the other side of housing 26. Within male luer 30 there resides a plug 32 of porous, hydrophobic material such as polytetrafluoroethylene or polyolefin for the purpose of preventing the flow of blood from passing into the rest of set 10, while allowing air within the system to pass therethrough. Also, porous plug 32 serves to damp the pressure pulse that is transferred from the patient's cardiovascular system through needle 18 into the respective lumens of connected tubes 20 and 11, so that the pressure pulse within lumen 34 of pressure tube 11 is significantly reduced from the normal pressure fluctuation of about 50 mm. of mercury, down for example to a fluctuation on the order of 5 mm. of mercury, which pressure is then sensed by gauge 12. Specifically, porous plug 32 may be porous, high density polyethylene of about 25 micron pore size.

Additionally, housing 26 carries a conventional and commercially available bacteria blocking, hydrophilic, porous membrane filter 36, to preserve sterility within fistula set 14 even though connected with the nonsterile pressure gauge 12 and the set 10. Filter 36 can protect sterility of fistula set 14 as cannulation takes place.

Set 10 is nonsterile in this particular embodiment. Filter 36 may comprise a 0.2 micron porous polytetrafluoroethylene membrane such as GORETEX™.

Further in accordance with this invention, lumen 34 of pressure tubing 11 may be of substantially reduced diameter, typically being no more than about ¼ or ⅓ the outer diameter of tubing 11. Typically, lumen 34 may have a diameter of about 0.5 to 1 mm. The outer diameter of tubing 12 may be typically 3 to 4 mm. Because of this, the total lumen volume of pressure set 11, including the volume of connectors 15, 16 and the volume within gauge 12 that is accessible to pressurized air, may be substantially less that the total lumen volume of the first tube 20, specifically the fistula set 14.

Thus, as blood is allowed to enter into the connected systems through needle 18, with the interior of the system being sealed, the pressurized blood advances through fistula tubing 20, compressing the air in the respective lumens of tubings 20 and 11 until the compressed air pressure equals the blood pressure, which pressure typically naturally oscillates as described above. Because the volume of air in pressure tubing 11 and gauge 12 is less than the volume of air in fistula set 14, the length of set 10 may be substantially longer for convenience of gripping gauge 12, while at the same time pressurized blood in fistula set tubing 20 will not normally advance into contact with plug 32 of housing 26 during pressure reading to assure accuracy of the reading. Pressure set 10 can be reused along with pressure gauge 12 for a number of times.

Thus, the connected system provides an easy readout of pressure in the fistula prior to or after a procedure such as hemodialysis, where the fistula is in use anyway, requiring the use of only gauge 12 and set 10, both of which are reusable, plus a housing 26. Housing 26 may also serve to protect sterility of the fistula when it is not connected either to set 10 or to an arterial or venous set for hemodialysis.

At the end of pressure testing, fistula set 14 is self-primed in this embodiment. When the connection between connectors 15, 28 is broken, venous pressure drives blood in tube 20 outwardly into contact with plug 32, where flow stops. Tube 20 is clamped; housing 26 is removed; and connection is made between primed fistula set 14 and an arterial or venous blood set for hemodialysis or other procedure.

Similar sets may be used in accordance with this invention for determining the pressure in an implanted vascular catheter or another implanted access device in a patient for any desired reason.

Referring to FIG. 3, pressure gauge 12 may be connected to the same or a similar fistula set 14 by a modified version of the flexible, tubular set 10a of this invention. Set 10a may be basically similar in form to set 10, comprising flexible tubing 11a with a reduced diameter bore 34a as in the previous embodiment. Conventional connector 16a can connect to pressure gauge 12 in a manner similar to the previous embodiment. The opposed connector 14a may be a male luer lock connector as in the previous embodiment. However, in this embodiment, porous hydrophobic plug 32a may be positioned within the lumen 42 of connector 14a, rather than being positioned in a separate housing like housing 26. Thus, set 10a may be provided to the user in sterile condition, being contained in a conventional, sterile package. Since set 10a is sterile, there is no need for a bacteria blocking membrane similar to membrane 36 of the previous embodiment, because set 10a remains dry, and is blocked from contact with blood by the presence of microporous plug 32a.

Set 10a connects directly with female luer connector 24 of fistula set 14 at one end, and connects with pressure gauge 12 through connector 16a at the other end, to provide a closed pressure transfer passageway from the patient's fistula, accessed by fistula set 14, to pressure gauge 12. Pressure pulses are damped by porous plug 32a to provide an easy, convenient pressure reading for monitoring the onset of stenosis in the patient's fistula. Then, the sterile connection between connectors 14a and 24a may be broken, and fistula set 14 may be connected with a conventional arterial or venous hemodialysis set for the hemodialysis process.

Also, because of the constricted lumen 34a in set 10a, set 10a can be of a convenient length, so that gauge 12 is easily handled and read at an appropriate level at about the heart of the patient, while the internal volume of the lumen 46 of fistula set 14 is still greater than the internal volume of lumen 34a and the respective connectors 14a, 16a. Thus, upon displacement of air in the connected lumens and advancement of blood into fistula set 14, the pressure increase occurs rapidly to match the pressure in the blood before the fistula set 14 fills with blood, so that blood does not enter into contact with plug 32a.

The above has been offered for illustrative purposes only, and is not intended to limit the scope of the invention of this application, which is as defined in the claims below.

That which is claimed:

1. A flexible, tubular set in connection between a pressure gauge and a tubular connection with the vascular system of a patient, said set comprising pressure tubing having a connector at each end, said tubing having a single lumen of a diameter which is no more than about one third of the outer diameter of said tubing.

2. The set of claim 1 which connects to a microporous member to block the flow of blood through at least part of said tubing, while permitting the passage of air through said tubing, and to suppress the passage of pressure oscilliations through said tubing.

3. The set of claim 2 which carries a microporous member capable of preventing the passage of bacteria therethrough.

4. The set of claim 2, connected at one end to a first tube for connection to the vascular system of a patient, said pressure tubing having a total lumen volume that is substantially less than the total lumen volume of said first tube.

5. The set of claim 4, in which said pressure tubing has a length that is greater than the length of said first tube.

6. The set of claim 4 in which said first tube comprises a fistula set.

7. The set of claim 1, connected at one end thereof to a fistula set and connected at the other end thereof to a pressure guage.

8. A flexible tubular set in connection between a pressure gauge and a tubular connection with the vascular system of a patient, said set comprising pressure tubing having a connector at each end, said tubing having a single lumen extending from end to end, and a microporous member capable of preventing the passage of bacteria therethrough, said pressure tubing having means for suppressing the passage of pressure oscillations through said tubing.

9. The set of claim 8 in which said means for suppressing said pressure oscillations comprises a microporous member.

10. The set of claim 9 in which said microporous member is capable of preventing the passage of bacteria therethrough and further blocks the flow of blood through at least part of said pressure tubing while permitting the passage of air through said tubing.

11. The set of claim 10, connected at one end thereof to a fistula set and connected at the other end thereof to a pressure gauge.

12. The set of claim 8, in which said means for suppressing pressure oscilliations is manually separably connectable with said pressure tubing.

13. The set of claim 12, connected at one end to a first tube in connection to the vascular system of a patient, said pressure tubing having a total lumen volume that is substantially less than the total lumen volume of said first tube.

14. The set of claim 13 in which said pressure tubing has a length that is greater than the length of said first tube.

15. The set of claim 8 in which said means for suppressing the passage of pressure oscillations through said tubing comprises a microporous member capable of reducing the magnitude of pressure fluctuation by about 90%.

16. The set of claim 15, in which said microporous member comprises a porous plug having a length greater than its width.

17. The set of claim 8 in which said means for suppressing said pressure oscillations comprises a second microporous member, said second microporous member comprising a plug of microporous material having a length greater than its width.

18. The method of measuring access pressure through a first tube which is connected to the vascular system of a patient, which method comprises:
connecting one end of pressure tubing to an outer end of said first tube with a member blocking the flow of blood through at least part of said pressure tubing, while permitting the passage of air therethrough, to attenuate pressure pulses through said tubing; connecting the other end of said pressure tubing to a pressure gauge, and reading pressure by the gauge.

19. The method of claim 15 in which the internal volume of said pressure tubing is less than the internal volume of said first tube, whereby pressurized blood entering said first tube as said pressure is read does not naturally advance completely through said first tube.

20. The method of claim 18, in which the length of said pressure tubing is greater than the length of said first tube.

21. The method of claim 18 in which said member is a microporous member.

22. A connector housing for a tubular blood set system, which comprises:
a housing which defines a pair of housing connectors, each for connection with connectors of blood flow conduits, and a flow path within said housing extending between said housing connectors, a first porous, hydrophobic barrier member for preventing blood flow through said flow path while permitting the flow of air therethrough in a manner that dampens blood pressure pulses; said housing also having means for blocking the passage of microorganisms through said flow path.

23. The housing of claim 22 in which said first porous barrier member comprises a porous plug of about 25 micron pore size and a length greater than its width.

24. The housing of claim 22 in which said means for blocking the passage of microorganisms comprises a porous, hydrophobic membrane having a pore size of about 0.2 micron.

25. The housing of claim 24 in which said first porous barrier member comprises a porous plug of about 25 micron pore size and a length greater than its width.

26. A connector housing for a tubular blood set system, which comprises:
a housing which defines a pair of housing connectors, each for connection with connectors of blood flow conduits, and a flow path within said housing extending between said housing connectors, a first, porous hydrophobic barrier member for preventing blood flow through said flow path while permitting the flow of air therethrough in a manner that dampens blood pressure pulses, said housing also comprising a microorganism blocking, porous, hydrophobic membrane spaced from the barrier member in said flow path.

27. The housing of claim 26 in which said porous barrier member comprises a porous plug of about 25 micron pore size and a length greater than its width.

28. The housing of claim 26 in which said porous hydrophobic membrane has a pore size of about 0.2 micron.

29. A flexible tubular set for connection between a pressure gauge and a tubular connection with the vascular system of a patient, said set comprising pressure tubing having a connector at each end, said tubing having a single lumen extending from end to end, and a microporous member capable of preventing the passage of bacteria therethrough, said pressure tubing also comprising a microporous member for suppressing the passage of pressure oscillations through said tubing.

30. The set of claim 29 in which a pair of said microporous members are present, and said microporous members further block the flow of blood through at least part of said pressure tubing while permitting the passage of air through said tubing.

31. The set of claim 29 in which said pressure tubing has a lumen with a diameter which is typically no more than about ⅓ of the outer diameter of the tubing.

* * * * *

UNITED STATES PATENT AND TRADEMARK OFFICE
CERTIFICATE OF CORRECTION

PATENT NO.    : 6,346,084 B1                                    Page 1 of 1
DATED         : February 12, 2002
INVENTOR(S)   : William H. Schnell et al.

It is certified that error appears in the above-identified patent and that said Letters Patent is hereby corrected as shown below:

Column 6,
Line 1, "claim 15" should be -- claim 18 --.

Signed and Sealed this

Twenty-fourth Day of September, 2002

Attest:

Attesting Officer

JAMES E. ROGAN
Director of the United States Patent and Trademark Office